United States Patent [19]
Trentham et al.

[11] Patent Number: 5,399,347
[45] Date of Patent: Mar. 21, 1995

[54] METHOD OF TREATING RHEUMATOID ARTHRITIS WITH TYPE II COLLAGEN

[75] Inventors: David E. Trentham, North Quincy; Howard L. Weiner, Brookline; David A. Hafler, West Newton, all of Mass.

[73] Assignee: Autoimmune, Inc., Lexington, Mass.

[21] Appl. No.: 951,565

[22] Filed: Sep. 25, 1992

Related U.S. Application Data

[63] Continuation-in-part of Ser. No. 460,852, Feb. 21, 1990, which is a continuation-in-part of Ser. No. 596,936, Oct. 15, 1990, which is a continuation-in-part of Ser. No. 65,734, Jun. 24, 1987, abandoned.

[51] Int. Cl.⁶ .................. A61K 39/00; A61K 37/02; A61K 37/12
[52] U.S. Cl. ..................... 424/184.1; 424/185.1; 514/2; 514/8; 514/21; 514/825
[58] Field of Search ............ 424/184.1, 185.1; 514/2, 8, 12, 13, 21, 825; 930/20; 530/356, 324, 325, 868

[56] References Cited

U.S. PATENT DOCUMENTS 4,804,745 2/1989 Koepff et al. .................. 530/356

OTHER PUBLICATIONS

Thompson et al (1985) Clin. Exp. Immunol 64: 581–586.
Zhang et al (1990 Apr. 26, 1990) FASEBJ. 4(7): Abst No. 3264.
Phadke et al (1984) Arthritis and Rheumatism 27(7): 797–806.
Wells, H., *J. Infect. Dis.* 9:147 (1911).
Ngan, J. et al., *J. Immunol.* 120:861 (1978).
Gautam, S. C. et al., *J. Immunol.* 135:2975 (1985).
Titus, R. et al., *Int. Arch. Allergy Appl. Immunol.* 65:323 (1981).
Higgins, P. J. et al., *J. Immunol.* 140:440 (1988).
Lider, O. et al., *J. Immunol.* 142:748 (1989).
Bitar, D. M. et al., *Cell. Immunol.* 112:364 (1988).
Nagler-Anderson, C. et al., *Proc. Natl. Acad. Sci. USA* 83:7443 (1986).
Thompson, H. S. G. et al., *Clin. Exp. Immunol.* 64:581 (1985).
Swierkosz, J. E. et al., *J. Immunol.* 119:1501 (1977).
Lando, Z. et al., *Nature* 287:551 (1980).
Lando, Z. et al., *J. Immunol.* 126:1526 (1981).
Sriram, S. et al., *Cell. Immunol.* 75:378 (1983).
Alvord, E. C. et al., *Annals of Neurol.* 6:461 (1979).
Alvord, E. C. et al., *Annals of Neurol.* 6:469 (1979).
Alvord, E. C. et al., *Annals of Neurol.* 6:474 (1979).
Traugott, U. et al., *J. Neurol. Sci.* 56:65 (1982).
Raine, C. S. et al., *Lab. Invest.* 48:275 (1983).
McKenna, R. et al., *Cell. Immunol.* 81:391 (1983).
Strejan, G. et al., *Cell. Immunol.* 84:171 (1984).
McKenna, R. et al., *Cell. Immunol.* 88:251 (1984).
Burns, J. et al., *Neurology* 36:92 (1986).
Belik, Y. et al., *Vopr. Med. Khim.* 24:372 (1978).
Mowat, A. M., *Immunol. Today* 8:93 (1987).
Trentham, D. E. et al., *J. Clin. Invest.* 66:1109 (1980).
Myers, L. K. et al., *J. Exp. Med.* 170:1999 (1989).
Myers, L. K. et al., *J. Immunol.* 143:3976 (1989).
Kardys, E. et al., *J. Immunol.* 127:862 (1981).
Holoshitz, J. et al., *J. Immunol.* 131:2810 (1983).
Mokhtarian, F. et al., *Nature* 309:356 (1984).
Braley-Mullen, H. et al., *Cell. Immun.* 39:289 (1978).
McDermott, J. R. et al., *J. Neurol. Sci.* 46:137 (1980).
Raziuddin, S. et al., *J. Immunol.* 128:2073 (1982).
Alvord, E. C. et al., *Ann. N.Y. Acad. Sci.* 122:333 (1965).
Higgins, P. J. et al., *J. Neuroimmunol.* 16:77 (1987).
Higgins, P. J. et al., *Annals of Neurol.* 20:161, Abstract P154 (1986).
Whitacre, C. C. et al., *Abstr. 6th Int'l. Congr. Immunol.*, Toronto (Jul. 1986) (Distrib. to Registered Attendees Upon Request, May 1986).
Whitacre, C. C. et al., Titles of Workshop Presentations No. 615-09, *5th Int'l. Congr. of Immunol.* Kyoto, Japan (1983).
Schoen, R. T. et al., *J. Immunol.* 128:717 (1982).
Eylar, E. H., *Adv. Exp. Med. Biol.* 98:259 (1978).
Gonsette, R. E. et al., *J. Neurol.* 216:27 (1977).
Campbell, B. et al., *Arch. Neurol.* 29:10 (1973).

*Primary Examiner*—Kay K. A. Kim
*Attorney, Agent, or Firm*—Darby & Darby

[57] ABSTRACT

The present invention is directed to a method and pharmaceutical formulations for the treatment of autoimmune arthritis and animal models therefore in mammals, including humans, by the oral, enteral or by-inhalation administration of whole collagen protein or biologically active peptide fragments of collagen.

7 Claims, 4 Drawing Sheets

Effect of Feeding CII on AA

METHOD OF TREATING RHEUMATOID ARTHRITIS WITH TYPE II COLLAGEN

This patent application is a continuation-in-part of:

Weiner et al., U.S. patent application Ser. No. 460,852 filed Feb. 21, 1990, and Ser. No. 596,936, filed Oct. 15, 1990 (the former being the national stage of PCT Application No. PCT/US88/02139, filed Jun. 24, 1988, the latter being identical to PCT/US91/07542) which in turn are continuation-in-part applications of U.S. patent application Ser. No. 065,734 filed Jun. 24, 1987, now abandoned;

Weiner et al., U.S. patent application Ser. No. 454,806 filed Dec. 20, 1989 (now Ser. No. 08/053,356);

Weiner et al., U.S. patent application Ser. No. 487,732 filed Mar. 2, 1990 (now Ser. No. 08/202,677);

Weiner et al., U.S. patent application Ser. No. 809,206 filed Dec. 13, 1991 (abandoned), a continuation application of U.S. application Ser. No. 551,632 filed Jul. 10, 1990 (now Ser. No. 08/178,461), in turn a continuation-in-part application of U.S. patent application Ser. No. 379,778, filed Jul. 14, 1989, (now abandoned);

Weiner et al., U.S. patent application Ser. No. 595,468, filed Oct. 10, 1990 (now Ser. No. 08/235,121); and Weiner et al., U.S. patent application Ser. No. 843,752, filed Feb. 28, 1992.

The foregoing applications are incorporated by reference herein in their entireties.

FIELD OF THE INVENTION

The present invention pertains to treatment of autoimmune arthritis in humans. Specifically, the invention is directed to oral, enteral or by-inhalation administration of collagen or fragments or analogs to humans to induce specific suppression of the autoimmune response involved in rheumatoid and more generally in autoimmune arthritis. The invention is also directed to pharmaceutical formulations useful in the treatment of arthritis in humans comprising whole collagen, arthritis-suppressive peptide fragments thereof, and combinations of two or more of the foregoing.

BACKGROUND OF THE INVENTION

Collagen is the most common protein in the structural support of the human or mammalian body. Collagen's basic elemental unit is the tropocollagen protein. Tropocollagen is composed of three polypeptide chains of the same size. These chains are wound about each other forming a superhelical cable or a triple-stranded helical rod. Each of the three chains in tropocollagen consists of about a thousand amino acid residues.

Five different types of collagen proteins are currently recognized as distinct, differing in amino acid composition and length. Type I collagen is composed of two alpha-1(I) and one alpha-2 polypeptide chains. Type I collagen is mostly found in the supporting structure of skin tissue, tendon, bone and in the eye cornea. Type II collagen contains three polypeptide chains of the alpha-1(II) type and is found primarily in articular cartilage, within the intervertebral discs and in the vitreous body within the eye. Type III collagen is composed of three alpha-1(III) polypeptide chains and is found in tissues such as fetal skin, the cardiovascular system and reticular fibers in the eye. Type IV collagen has a mixture of two alpha-1(IV) and one alpha-2(IV) polypeptide chains and is primarily found in basement membranes. Finally, Type V collagen has two alpha-1 (V) and one alpha-2(V) polypeptide chains and is found, e.g. in placenta and skin. A comparison of the human alpha-1(II), bovine alpha-1(II) and bovine alpha-1(I) amino acid sequences is provided in Appendix A. The bovine sequences are partial.

Rheumatoid arthritis is a cell-mediated autoimmune disease, i.e. a condition where the immune system mistakenly perceives the body's own tissue as foreign and mounts an abnormal immune response against it. Rheumatoid arthritis is characterized by persistent inflammatory synovitis that causes destruction of cartilage and bone erosion, leading to structural deformities in the peripheral joints. Joints containing articular cartilage of which Type II collagen is a major component are particularly affected.

Rheumatoid arthritis is accompanied by joint swelling, inflammation, stiffness and pain especially upon flexing. In the advanced stages of arthritis, debilitating pain may result from even a slight movement of the joints. A substantial percentage of afflicted humans possess T-cells of the CD4+ type specifically reactive with collagen and/or have an abnormal humoral response against collagen.

Present treatment for arthritis involves use of nonspecific cytotoxic immunosuppressive drugs. These drugs suppress the entire immune system and are incapable of selectively suppressing the abnormal autoimmune response. This global restraint of the immune system over time increases the risk of infection. Non-limiting examples of such immunosuppressive drugs include methotrexate, cyclophosphamide, Imuran (azathioprine) and cyclosporin A.

Additionally, prolonged therapy with these nonspecific cytotoxic immunosuppressive drugs entails toxic side effects, including increased tendency towards development of certain malignancies, kidney failure, diabetes and liver function disorders. Moreover, cytotoxic immunosuppressive drug therapy merely slows down the progress of the disease, which resumes at an accelerated pace after the therapy is discontinued. For example, about six weeks after such a drug is discontinued, the patient deteriorates to the same stage as before the treatment was begun. In addition, effectiveness of these drugs is self-limiting; they gradually cease being effective after about 2–5 years.

Steroid compounds such as prednisone and methylprednisolone (which are also non-specific immunosuppressive and anti-inflammatory drugs) are also used for symptomatic relief. Steroids also have significant toxic side effects associated with their long term use.

Thus, current treatments for arthritis are of limited efficacy, involve significant toxic side effects, and cannot be used indefinitely. Rheumatoid arthritis afflicts over 2 million individuals in the United States in any given year. Accordingly, there is an acute need for novel treatments and for novel therapeutic compositions for human autoimmune arthritis that do not suffer from one or more of the drawbacks identified above.

An alternative treatment for arthritis is the oral antigen tolerization therapy proposed by the present inventors. It involves the oral, enteral, or by-inhalation administration of one or more tissue-specific antigens (i.e. antigens occurring only in the tissue under autoimmune attack) which have the ability to suppress the autoimmune response responsible for a particular autoimmune disease specifically, thus leaving other immune functions essentially intact.

The antigens useful in this approach generally include autoantigens, i.e. tissue-specific antigens that are themselves the subject of autoimmune attack. Bystander antigens, which are also tissue-specific (but are not the target of autoimmune attack) also possess the ability to elicit suppressor T-cells which are targeted to the afflicted tissue where they exert their immune suppressive activity via the release of transforming growth factor-beta (TGF-$\beta$). TGF-$\beta$ in turn down-regulates all immune cells concentrated in the vicinity of the afflicted tissue, thereby suppressing immune responses in that locality. Bystander antigens include without limitation portions of autoantigens that (i) are not themselves the target of autoimmune attack and (ii) possess the requisite suppressive activity via elicitation of suppressor T-cells.

Prior to the work of the present inventors, oral antigen tolerance therapy for arthritis had been tried only on artificially induced arthritis-like diseases in animals (adjuvant arthritis and collagen-induced arthritis).

Regardless of the correlation that may exist between human autoimmune arthritis and its animal (rodent) models, oral, enteral or inhalatory antigen tolerization had never been tried in humans afflicted with arthritis. Moreover, in the rodent models, collagen was shown only to prevent disease induction and had no or minimal effect on pre-induced disease.

The role of collagen in arthritis and its models, has been the subject of many publications, including some describing the oral use of collagen to prevent disease induction in the rodent model. A chronological summary of the state of the art follows.

Collagen was shown to be the tissue under autoimmune attack in the artificially induced cell-mediated autoimmune arthritis model by Trentham, D. E. et. al., *J. Clin. Invest.*, 66:1109–1117, November, 1980. The authors showed that both humoral and cellular autoimmunity to type I and type II collagen is a feature of both adjuvant- and collagen-induced arthritis in rats.

Schoen, R. T. et. al., *J. Immunol.* 128:717–719, February, 1982, found that type I collagen, unlike type II collagen, coupled artificially to naive spleen cells and injected into normal animals was ineffectual in preventing inducement of arthritis-like disease.

Thompson, H. S. G. et. al., *Clin. Exp. Immunol.*, 64:581–586, 1986, reported resistance to induction of a polyarthritis model in rats after prophylactic intragastric administration of soluble type II collagen protein (2.5 or 25 $\mu$g/g body weight/day for 5 days). The lower amount, 2.5 $\mu$g/g, was slightly more effective.

Nagler-Anderson, C. et. al., *Proc. Natl. Acad. Sci. USA*, 83:, October, 1986, pp. 260–262, that prophylactic intragastric administration (500 $\mu$g/mouse/12 times in 6 weeks) of undenatured soluble type II collagen was found to suppress inducement of arthritis in DBA/1Lac J mice by challenge with an adjuvant and collagen mixture.

Myers, L. K. et. al., *J. Immunol.*, 143:3976–3980, December, 1989, that the intravenous administration of type II but not type I collagen protein would confer resistance to subsequently induced arthritis-like disease in animal models. In a subsequent publication, the same group, *J. Exp. Med.*, 170:1999–2010, December, 1989, cite three other references for the same proposition: Schoen et. al., Supra; Cremer et. al., *J. Immunol.*, 87:2995, 1983; and Englert et. al., *Cell. Immunol.*, 87:357, 1984.

In this same *J. Exp. Med.* publication the authors state that they have identified a fragment of chicken type II collagen (CB11 corresponding to amino acid residues 122–147) which upon intravenous administration to mice prior to challenge conferred protection against collagen induced arthritis. This peptide had the sequence P-T-G-P-L-G-P-K-G-Q-T-G-E-L-G-I-A-G-F-K-G-E-Q-G-P-K [SEQ ID NO: 1].

In summary, the most relevant art teachings are limited as follows:
  experiments were conducted solely on induced animal models;
  animals tested were limited to species susceptible to disease induction;
  the treatment was ineffective against already induced disease;
  intravenous administration of type I collagen was ineffective to prevent disease inducement.
  one immunosuppressive epitope of chick type II collagen intravenously administered to mice was identified.

OBJECTS OF THE INVENTION

An object of the invention is to provide a treatment for human autoimmune arthritis including without limitation rheumatoid arthritis and polychondritis.

Another object of the invention is to specifically suppress the abnormal immune response attacking cartilage and resulting in subchondral bone deterioration in human beings.

An additional object of the invention is to provide a clinical treatment for autoimmune arthritis without undesirable side effects in human beings, such as one or more of those associated with conventional therapy.

A further object of the invention is to significantly reduce symptoms associated with arthritis such as one or more of swelling, inflammation, stiffness and pain of the joints in mammals, particularly human beings.

Yet another object of the invention is to provide pharmaceutical formulations useful in the treatment of human rheumatoid arthritis.

SUMMARY OF THE INVENTION

One or more of the foregoing objects are achieved in a therapeutic treatment for autoimmune arthritis in humans by providing pharmaceutical formulations for oral, enteral or by-inhalation administration comprising at least one of collagen protein or a peptide fragment thereof or analogs of the foregoing with or without a synergist in an effective amount and by providing methods for treating such arthritis comprising the oral, enteral or by-inhalation administration to afflicted humans of said formulations in effective amounts.

DETAILED DESCRIPTION OF THE INVENTION

Figure 1:
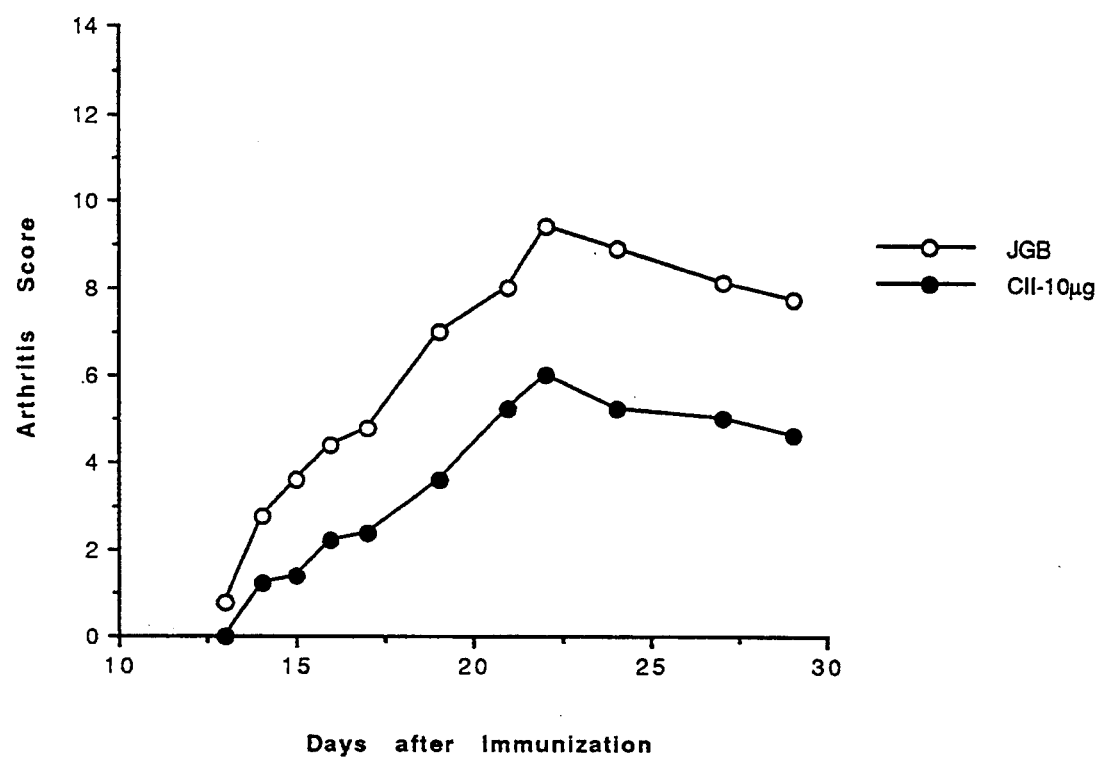
FIG. 1 shows the suppressive ability of whole collagen.

All patent applications, patents and literature references cited in this specification are hereby incorporated by reference in their entirety. In case of inconsistency, the present description including the definitions and interpretations contained herein will prevail.

DEFINITIONS

Each of the following terms used in this disclosure shall have the meaning ascribed to it below:

"Treatment" includes both prophylactic measures to prevent the onset and appearance of arthritis as well as to prevent the onset and appearance of the abnormal immune response against the body's own cartilage involved in arthritis. The term also encompasses the suppression or mitigation of the abnormal (cell and/or humoral) immune response to the body's own collagen or more generally cartilage as well as the alleviation or elimination of clinical symptoms after the onset (i.e. clinical manifestation) of autoimmune arthritis.

"Mammal" is any organism having an immune system and being susceptible to an autoimmune disease. This term encompasses human beings.

"Autoimmune disease" is defined as a malfunction of the immune system of mammals, in which the immune system fails to distinguish between foreign substances within the mammal and/or autologous tissues or substances and, as a result, treats autologous tissues and substances as if they were foreign and mounts an immune response against them.

"Active fragment" of type I, type II or type III collagen protein describes any synthetic peptide or polypeptide construct consisting essentially of one or more partial amino acid sequences of collagen protein and possessing the ability to suppress or eliminate T-cell mediated or T-cell dependent autoimmune response to collagen, upon oral, enteral or by-inhalation administration. This definition thus excludes fragments of the collagen protein that do not produce suppression of the autoimmune response in vitro, e.g. in a lymphocyte proliferation assay or in vivo, e.g. in a rodent model or in a human.

"Active analogs" of type I, type II or type III collagen protein include compounds that are structurally related to type I, type II or type III collagen protein or to active fragments thereof. As such, the term includes, without limitation, any combination of alpha 1 (I or II) and alpha 2 (I) tropocollagen polypeptide chains or fragments thereof possessing the ability to eliminate or suppress T-cell mediated or T-cell dependent autoimmune response to collagen, upon oral, enteral or by-inhalation administration. The term "analog" also encompasses any polypeptide which differs from the amino acid sequence of alpha 1(I, II or III) and/or alpha 2(I) tropocollagen polypeptide chains by one or more amino acids while still retaining substantially equivalent ability to suppress arthritis immune response.

"Synergists" are defined as substances which augment or enhance the suppression of the clinical and/or histological manifestation of arthritis when administered orally, enterally or by inhalation in conjunction with the administration of collagen protein or at least one of their active fragments or their analogs. As used in the preceding sentence, and elsewhere in this specification, "in conjunction with" (also referred to herein as in association with) means before, substantially simultaneously with or after oral, enteral or by-inhalation administration of collagen protein or at least one of its active fragments or their active analogs. Naturally, administration of the conjoined substance should not precede nor follow administration of collagen by so long an interval of time that the relevant effects of the substance administered first have worn off. Therefore, synergists should usually be administered within about 24 hours before or after collagen protein or its biologically active peptide fragments and preferably within about one hour.

"Oral" administration includes oral, enteral or intragastric administration. Oral administration which does not bypass the stomach is preferred.

The present invention is based on the discovery and confirmation that oral, enteral or by-inhalation administration of type I, type II or type III collagen or its biologically active peptide fragments in small amounts is a particularly effective means of suppressing T-cell-mediated or T-cell dependent autoimmune and particularly rheumatoid arthritis in humans. Thus, as demonstrated below, the simple method of administration, orally, enterally or by inhalation, of at least one of type I, type II or type III collagen or active fragments or analogs of at least one of them, as taught by the invention, is an effective treatment to suppress the development of arthritis. Furthermore, the compositions and method of the invention do not have the drawbacks described above and associated with prior art therapeutic or palliative agents and techniques.

Oral, enteral or by-inhalation induced tolerance is dose-dependent over a broad range of oral, enteral and inhalant dosages. However, there are minimum and maximum effective dosages. As is understood by one skilled in the art, this means that suppression of both clinical and histological symptoms of arthritis occurs within a specific dosage range which varies as a function of the type of the collagen protein administered, whether it is whole protein or discrete peptide fragment(s) or analog(s), as well as the solubility and purity of the peptides or polypeptides. Moreover, the age, sex and physical condition of the patient, as well as other concurrent treatments being administered also have a bearing on the effective dosage of collagen protein for treatment. Consequently, adjustment and refinement of the dosages used and administration schedules must be determined based on these factors, and may need to be determined experimentally. Such determinations, however, require no more than routine experimentation. Type II collagen and its fragments and analogs are most preferred.

Generally, the preferred way to accomplish suppression of the immune responses against the human body's collagen in arthritis is the administration, orally, enterally or by inhalation of purified or highly purified water-soluble whole type I, type II or type III collagen protein or its biologically active peptide fragment(s) in an amount from about 0.05 to about 10 mg/day. The administration of collagen or its biologically active peptide fragments may be accomplished in a single dose form or multiple dose form. Preferably, the whole collagen protein is administered at dosage from 0.1 to 1 milligram per day and this dosage is particularly preferred for type II collagen. The foregoing dosages can be easily extrapolated to other types of collagen as well as to fragments and analogs, in light of the present disclosure and in light of the fact that in rats a type II collagen amount as small as 3 micrograms/day was immunosuppressive, the preferred amount was 30 micrograms/day and an amount of 300 micrograms per day was too high as it lost effectiveness. Z. J. Zhang, et al., *J. Immunol.* 145:2489-2493, 1990.

In addition, synergists can be conjoined in the treatment to enhance the effectiveness of the above. Non-limiting examples of synergists for use in the present invention include bacterial lipopolysaccharides from a wide variety of gram negative bacteria such as various subtypes of *E. coli* and Salmonella (LPS, Sigma Chemical Co., St. Louis, Mo.; Difco, Detroit, Mich.; BIOMOL Res. Labs., Plymouth, Pa.), Lipid A (Sigma Chemical Co., St. Louis, Mo.; ICN Biochemicals, Cleveland, Ohio; Polysciences, Inc., Warrington, Pa.) and immunoregulatory lipoproteins, such as peptides covalently linked to tripalmitoyl-S-glycarylcysteinyl-seryl-serine ($P_3C55$) which can be obtained as disclosed in Braun, V., *Biochim, Biophys. Acta* 435:335-337, 1976. LPS is preferred and Lipid A is particularly preferred. Lipid A is particularly preferred for use in the present invention because it is less toxic than the entire LPS molecule. LPS for use in the present invention can be extracted from gram negative bacteria and purified using the method of Galanes et. al. (*Eur. J. Biochem.* 9:245, 1969) and Skelly, R. R., et. al., (*Infect. Immun.* 23:287, 1979).

FORMULATIONS

In another aspect, the present invention also provides oral pharmaceutical formulations for treating mammals suffering from arthritis comprising an amount of whole collagen protein or its biologically active peptide fragment(s) (as described below) or analogs effective to suppress autoimmune arthritis of an animal model thereof. The formulations optionally further comprise a synergist as disclosed in co-pending U.S. patent application Ser. No. 487,732, filed Mar. 2, 1990 in an amount effective (in conjunction with the tolerizing antigen of the present invention) to treat the clinical symptoms of arthritis. Synergists, when administered in conjunction with whole type I, type II or type III collagen protein or its active peptide fragment(s) or analog(s), cause an increase of cytokines PGE (prostaglandin-E) and IL-4 (interleukin-4) in the vicinity of the collagen tissue under immune attack. Liquid aqueous formulations containing soluble collagen, preferably type II or type III and most preferably type II with an acid pH (e.g. 0.01M acetic acid) are preferred. The pH adjusting agent can be any pharmaceutically acceptable acidic agent and a buffer may also be included. The preferred pH range is 4 to 5. A solid composition can also be preferably administered, after it is dissolved in an acidic aqueous medium such as 0.01M acetic acid.

Throughout this discussion, it will be understood that any clinically or statistically significant attenuation of even one symptom of arthritis pursuant to the treatment of the present invention is within the scope of the invention. Such symptoms include joint tenderness, joint swelling, AM stiffness, grip strength reduction, slowness in walking. In normal individuals, the first three aforementioned symptoms are absent, a 50 foot walk should take less than 9 seconds and adult grip strength should be more than 200 mm Hg (although strength varies with age, sex and physical condition). Clinically significant attenuation means perceptible to the patient (as in the case of tenderness or general well-being) and/or to the physician (as in the case of joint swelling). For example, a perceptible difference in swelling or tenderness in even one arthritic joint is significant. Absence of swelling or tenderness in a previously affected joint is most significant. For those parameters that are capable of measurement, a difference of 1 second in the case of the 50-foot walk, or 5 mm Hg in the case of strength or 15 minutes in AM stiffness is significant.

In addition, the ability to refrain from administration of cytotoxic drugs or other anti-inflammatory agents is also significant. Thus, even if the patient did not improve he/she is still deemed to have received a significant benefit if cytotoxic drugs and/or anti-inflammatory agent administration did not have to resume, and the patient is kept in the same condition or progressive disease state as with these conventional drugs.

Each oral, enteral or inhalable formulation according to the present invention may additionally comprise inert constituents including pharmaceutically acceptable carriers, diluents, fillers, solubilizing or emulsifying agents, and salts, as is well-known in the art. For example, tablets may be formulated in accordance with conventional procedures employing solid carriers well-known in the art. Capsules employed in the present invention may be made from any pharmaceutically acceptable material, such as gelatin, or cellulose derivatives. Sustained release oral delivery systems and/or enteric coatings for orally administered dosage forms are also contemplated, such as those described in U.S. Pat. No. 4,556,552, issued Dec. 3, 1985; U.S. Pat. No. 4,309,404, issued Jan. 5, 1982; and U.S. Pat. No. 4,309,406, issued Jan. 5, 1982.

Examples of solid carriers include starch, sugar, bentonite, silica, and other commonly used carriers. Further non-limiting examples of carriers and diluents which may be used in the formulations of the present invention include saline, syrup, dextrose, and water.

It will be appreciated that unit content of active ingredient(s), whole collagen or its active fragment(s) or analog(s), contained in an individual dose of each dosage form need not in itself constitute an effective amount, since the necessary effective amount can be reached by administration of a plurality of dosage units (such as capsules or tablets or combinations thereof). Administration of an effective dosage may be in a single dose form or in multiple dosage forms and it may be provided with an enteric coating and/or a sustained release mechanism, such as a degradable matrix or a reservoir.

Where whole collagen protein or its biologically active peptide fragment(s) are introduced orally or enterally, it may be mixed with other ingestible forms and consumed in solid, semi-solid solution, suspension, or emulsion form. It may also be mixed in conjunction or alternatively with pharmaceutically acceptable carriers, flavor enhancers, water, suspending agents and emulsifying agents.

The effective amount of a synergist, e.g., LPS or Lipid A, may be administered in conjunction with whole type I, type II or type III collagen or its active fragment(s) or analog(s) the amount of synergist being in the range of about 0.01 mg and 100 mg per day and preferably between about 0.1 mg and 10 mg per day.

In an alternative preferred embodiment of the present invention the pharmaceutical formulations or dosage forms of the present invention can also be administered to humans suffering from arthritis by inhalation, preferably in aerosol form. The inhalation mode of administration is preferably not through the nasal mucosa but through the bronchial and pulmonary mucosa. It is expected that lower amounts of whole collagen or its active fragment(s) or analog(s) of the present invention will be required using aerosol administration for treating arthritis as it has been found when treating adjuvant arthritis with collagen as disclosed in co-pending U.S. patent application Ser. No. 454,486 filed Dec. 20, 1989. The amounts of whole collagen or its active peptide fragment(s) or analog(s) of the present invention which may be administered in an aerosol dosage form would be between about 0.01 milligram and about 5 milligrams per day (and preferably 0.01 to 0.5 mg per day) and may optionally include a synergist in amounts ranging between about 0.01 and about 100 mg per day and may be administered in single dosage form or multiple dosage forms. The exact amount to be administered may vary depending on the state and severity of a patient's disease and the physical condition of the patient.

The aerosol pharmaceutical formulations of the present invention may include, as optional ingredients, pharmaceutically acceptable carriers, diluents, solubilizing and emulsifying agents, and salts of the type that are well-known in the art. Nonlimiting examples of such substances include normal saline solutions, such as physiologically buffered saline solutions, and water.

The route of administration of whole collagen or its active fragment(s) or analog(s) according to this alternate embodiment of the present invention is in an aerosol or inhaled form. The whole collagen or its active fragment(s) with or without a synergist can be administered as dry powder particles or preferably as an atomized aqueous solution suspended in a carrier gas (i.e. air or $N_2$). Preferred aerosol pharmaceutical formulations may comprise, for example, a physiologically-acceptable buffered saline solution containing between about 0.01 milligram and up to about 5 (preferably up to about 0.5) milligrams of whole collagen or its active fragment(s) or analog(s) according to the present invention.

Dry aerosol in the form of finely divided solid particles of whole collagen or its biologically active peptide fragment(s) that are not dissolved or suspended in a liquid are also useful in the practice of the present invention. The whole collagen or its active fragment(s) or analog(s) may be in the form of dusting powders and comprise finely divided particles having an average particle size of between 1 and 5 microns, preferably between 2 and 3 microns. Finely divided particles may be prepared by pulverization and screen filtration using techniques well known in the art. The particles may be administered by inhaling a predetermined quantity of the finely divided material, which can be in the form of a powder.

Specific non-limiting examples of the carriers and/or diluents that are useful in the aerosol pharmaceutical formulations of the present invention include water and physiologically-acceptable buffered saline solutions such as phosphate buffered saline solution pH 7.0–8.0. Additional non-limiting examples of suitable carriers or diluents for use in the aerosol pharmaceutical formulations or dosage forms of the present invention are disclosed in U.S. Pat. No. 4,659,696 issued Apr. 21, 1987; U.S. Pat. No. 4,863,720 issued Sep. 5, 1989; and U.S. Pat. No. 4,698,332 issued Oct. 6, 1987.

The pharmaceutical formulations of the present invention may be administered in the form of an aerosol spray using, for example, a nebulizer such as those described in U.S. Pat. No. 4,624,251 issued Nov. 25, 1986; U.S. Pat. No. 3,703,173 issued Nov. 21, 1972; U.S. Pat. No. 3,561,444 issued Feb. 9, 1971 and U.S. Pat. No. 4,635,627 issued Jan. 13, 1971. The aerosol material is inhaled by the subject to be treated.

Other systems of aerosol delivery, such as the pressurized metered dose inhaler (MDI) and the dry powder inhaler as disclosed in Newman, S. P. in *Aerosols and the Lung*, Clarke, S. W. and Davia, D., eds., pp. 197–224, Butterworths, London, England, 1984, can be used when practicing the present invention.

Aerosol delivery systems of the type disclosed herein are available from numerous commercial sources including Fisons Corporation (Bedford, Mass.), Schering Corp. (Kenilworth, N.J.) and American Pharmoseal Co. (Valencia, Calif.).

The present inventors have also discovered biologically active peptide fragment(s) of type II collage protein that induce suppression or arthritis in the animal model when orally administered. Most of these peptide fragments have not been disclosed or suggested before the present invention and none had been used as oral tolerizers before. Oral, enteral or by-inhalation administration of peptides with oral tolerizer activity is expected to be more convenient and/or specific in eliciting autoimmune suppression than administration of the entire collagen protein without risk of sensitizing the mammal to the autoimmune response inducing portions of the collagen protein(s). Additional immunosuppressive peptides can be identified by routine experimentation in light of the present specification, claims and figures.

T-cells from humans afflicted with rheumatoid arthritis can be collected from, e.g., peripheral blood and T-cells of the CD8+ type can be isolated and cloned. Those CD8+ T-cells that secrete TGF-$\beta$ in response to whole collagen can then be isolated, cloned, and used in an in Vitro assay to test for their ability to secrete TGF-$\beta$ (and/or another cytokine) when stimulated by (in the presence of) a collagen peptide fragment. The ability of these cells to secrete TGF-$\beta$ can be assessed by monitoring the suppression of proliferation of e.g. CD4+ collagen-reactive T-cells in the presence of whole collagen, e.g. in a transwell system. The collagen peptide fragments that stimulate CD8+ T-cells to secrete TGF-$\beta$ will be orally tolerogenic. Such experiments have been described in U.S. patent application Ser. No. 843,752 filed Feb. 28, 1992. A method for isolating and cloning human T-cells has been described in U.S. patent application Ser. No. 502,559, filed Mar. 30, 1990 and Allegretta, M. et al., *Science* 247:718–721, 1990.

The following are examples which are intended to illustrate the present invention without limiting its scope.

EXAMPLES

For the purposes of the two studies conducted and described below, the patient's arthritic state was measured utilizing several different criteria such as subjective pain, gross anatomical observations, timing of physical acts and subjective well-being as described by the patient. Gross anatomical observations included AM stiffness, grip strength and number of swollen joints and were made during monthly examinations by a physician of the arthritic joints before and during type I collagen treatment as compared with the same joints prior to treatment.

Monthly data measuring subjective pain involved applying gently pressure to each arthritic joint in turn by a physician and being told by the patient whether pain was experienced.

Morning stiffness data were based on the patient's experience and reports on how long it took for their arthritic joints to become physically limber. Additionally, grip strength for each hand was measured each month with a standard mercury sphygmomanometer with the cuff inflated to 20 mm Hg. Finally, the patients were timed to measure how many seconds were needed to complete a 50 foot walk.

Global assessment (P=poor; F=fair; G=good; VG=very good; and VP=very poor) was subjectively made by the attending physician. Progress was similarly subjectively assessed (B=better; W=worse; MB=medium better; MW=medium worse, S=same).

NSAID stands for "nonsteroidal antiinflammatory drugs"; RF stands for "rheumatoid factor"; ESR stands for "erythrocyte sedimentation rate"; HCT stands for "hematocrit"; bid stands for "twice a day"; qid and qd stand for "per day"; IA stands for "intra-joint".

Daily dosage of whole type II chick collagen protein consumed was 0.1 milligrams for the first month and 0.5 milligrams for each subsequent month of treatment.

EXAMPLE 1

Water-soluble purified whole chick Type II collagen protein was obtained from commercial sources; (Genzyme, Boston, Mass.) or was purified according to the procedure of Trentham, D. et al., *J. Exp. Med.* 146:857, 1977. Patients, LS, MF, NS and CO, suffering from arthritis were given a solution of whole type II collagen protein in 0.01M acetic acid 0.1 or 0.5 mg/ml collagen. The patients were instructed to consume daily on an empty stomach a predetermined volume corresponding to 0.1 milligrams for the first month of treatment and 0.5 mg to all subsequent months of treatment. Most of the patients added the predetermined amount of type II collagen protein to orange juice to maintain solubility and shortly consumed the mixture.

Collagen treatment was discontinued after three months if the patient reported (and if the physician agreed) a substantial improvement. However, type II collagen treatment was subsequently resumed when a patient reported a relapse into the arthritic state. Monthly data gathered for each of the above patients are summarized in Tables 1–4.

Table 1 is a summary of data gathered measuring the arthritic disease state of patient 1, LS a 30-year old female. Prior drug treatment of auranofin was discontinued during the present study. Surprising recovery from arthritis during the second month of collagen treatment prompted discontinuation of further therapy. Feldene (piroxicam) was administered during months 8 and 9 after collagen therapy initiation.

Substantial improvement was observed after the first month of treatment with whole type II collagen protein. Complete recovery was observed on the second month of treatment, but some weakness was still observed in the grip strength test. This muscular weakness may have been caused by the prolonged disuse and atrophy of the muscles from the arthritic pain of the joints. On the third month of treatment, there was residual arthritis observed in one joint of the right hand which remained swollen, tender to slight pressure, the source of morning stiffness, and the reason for a weakened right hand grip. However, the joints in the left hand remain free of arthritis and the 50 foot walk was normal.

Treatment was discontinued for three and a half months, but reinstated on the seventh month when the patient LS experienced a mild arthritic relapse involving six joints in both hands. Ambulatory motion was not affected by this relapse. The patient was able to complete the 50 foot walk in normal time.

Treatment was reinstated at the normal daily dose of 0.5 milligrams. Again, remarkable recovery from the arthritic disease state was observed within a month with only residual arthritis present in one right hand joint. Grip strength doubled from that observed during the relapse.

Treatment was continued for one more month where patient LS exhibited the highest grip strength for both hands observed during the study, in spite of the remaining one arthritic joint in the left hand. After three month of collagen treatment to address the relapse, further treatment was again discontinued. To date, four months have passed without patient LS succumbing to or manifesting any clinical evidence of arthritis, other than the limited manifestation on a single right hand joint. Grip strength for both hands has decreased slightly.

Table 2 is a summary of the progress of a female patient, MF (23) participating in the same study as patient LS. Prior drug treatment with methotrexate was discontinued. Patient MF was observed to experience a surprising freedom from symptoms after the first month of treatment with a daily dosage of 0.1 milligrams of whole type II collagen protein for one month followed by 0.5 mg for two months. Complete recovery was observed after the second month of treatment. No recurrence of arthritis was observed during the subsequent eleven months.

Table 3 summarizes the data for a third patient in the study, female NS (50). Methotrexate treatment was discontinued during this study. Remarkable diminution of symptoms was observed during the first month of treatment with collagen protein. The number of swollen joints was reduced from five to one, while all tender joints exhibited complete recovery. Morning stiffness was reduced from 120 minutes to 15 minutes, but only left hand grip strength showed a slight improvement. Residual swelling was observed on a single joint in the right hand, but complete recovery was observed in all other previously affected joints. Complete recovery was achieved during the third month of collagen treatment and further treatment was discontinued in spite of occasional arthritic flare-ups.

Table 4 encapsulates the data from patient CO (a female, 42) the last participant of this study. A more gradual recovery from arthritis was observed compared to other patients. Half of the affected joints recuperated from arthritic swelling and tenderness after the first month of collagen treatment, but morning stiffness, grip strength for both hands and length of time to complete the 50 foot walk remained substantially the same as the disease state. Remarkable recovery was recorded during the second month of treatment and almost complete recovery was observed during the third month, barring a single tender joint and some slight ambulatory weakness in the 50 foot walk test. Treatment was discontinued for the next two months, but was reinstated when patient CO experienced a partial relapse during the fifth month. After three more months of further treatment, patient CO has also completely recovered from arthritis, to date.

TABLE 1

PATIENT 1 (LS)*

| Month | 0 | 1 | 2 | 3 | 4 | 5 | 6 | 7 | 8 | 9 | 12 |
|---|---|---|---|---|---|---|---|---|---|---|---|
| date | 2/6/91 | 2/27/91 | 3/20/91 | 4/26/91 | | | 8/2/91 | 9/5/91 | 10/21/91 | 12/06/91 | 2/19/92 |
| Dose (mg) | | 0.1 | 0.5 | 0.5 | 0 | 0 | 0.5 | 0.5 | 0.5 | 0 | 0 |
| No. swollen joints | 7 | 2 | 0 | 1 | 1 | 1 | 6 | 1 | 1 | 1(__-R wrist) | 1(__-R wrist) |
| No. tender joints | 9 | 2 | 0 | 1 | 1 | 1 | 6 | 1 | 0 | 0 | 0 |
| AM stiffness (min) | 60 | 60 | 0 | 15 | 0 | 40–60 | 60 | 0 | 0 | 0 | 0 |
| Grip strength (mm) | | | | | | | | | | | |
| R | 60 | 55 | 88 | 72 | 120 | 86 | 70 | 75 | 140 | 102 | 130 |
| L | 45 | 43 | 85 | 110 | 95 | 128 | 85 | 145 | 148 | 102 | 122 |
| 50′ walk (sec) | 16 | 16 | 9 | 9 | 9 | 9 | 9 | 9 | 9 | 9 | 9 |
| Pt. global assessment | P | F | VG | G | VG | VG | F | G | VG | VG | VG |
| Progress | Same | MB | Same | Same | | | | B | B | B | Same |
| NSAID | | | + | + | − | − | − | + (Feldene) | + (Feldene) | + (1 mo) Tr. swelling R wrist; 4 mi/AM walks | − working full time |
| Other | | | | | | | | | | | |
| RF (date) | 2/13/91 neg | 3/6/91 neg | 3/28/91 equiv. | | 5/8/91 neg | | | | + 1:320 | | |

*Drug discontinued - Auranofin
Course I (initial) 2/6/91, final 5/5/91
Course II (initial) 8/2/91, final 11/2/91

TABLE 2

PATIENT 2 (MF)*

| Month | 0 | 1 | 2 | 3 | 4 | 5 | 6 | 7 | 8 | 12 |
|---|---|---|---|---|---|---|---|---|---|---|
| date | 2/21/91 | 3/27/91 | 4/18/91? | 5/29/91 | 6/26/91 | | | | 10/23/91 | 2/20/92 |
| Dose (mg) | | 0.1 | 0.5 | 0.5 | 0 | 0 | 0 | 0 | 0 | 0 |
| No. swollen joints | 3 | 1 | 0 | 0 | 0 | | | | 0 | 0 |
| No. tender joints | 3 | 0 | 0 | 0 | 0 | | | | 0 | 0 |
| AM stiffness (min) | 60 | 30 | 0 | 0 | 0 | | | | 0 | 0 |
| Grip strength (mm) | | | | | | | | | | |
| R | 240 | 244 | 245 | 280 | 280 | | | | 280 | 280 |
| L | 180 | 238 | 242 | 275 | 280 | | | | 280 | 280 |
| 50′ walk (sec) | 14 | 11 | 9 | 9 | 9 | | | | 9 | 9 |
| Pt. global assessment | P | G | G | VG | VG | | | | VG | VG |
| Progress | | B | B | B | B | | | | Same | Same |
| NSAID | + | + | + | − | − | | | | − | − |
| Other | | | | | | | | | | |
| RF (date) | 2/8/91 neg | 3/27/91 neg | | 5/29/91 neg | | | | | 10/29/91 neg | |

*Drug discontinued - MTX
Course I (initial) 2/22/91, final 5/26/91

TABLE 3

PATIENT 3 (NS)*

| Month | 0 | 1 | 2 | 3 | 4 | 5 | 6 | #10 |
|---|---|---|---|---|---|---|---|---|
| date | 4/4/91 | 5/2/91 | 6/6/91 | 7/1/91? | | 9/19/91 | 10/24/91 | 02/20/92 |
| Dose (mg) | | 0.1 | 0.5 | 0.5 | 0 | 0 | 0 | 0 |
| No. swollen joints | 5 | 1 | 1 | 0 | 0 | 1 | 1 | 1 |
| No. tender joints | 5 | 0 | 0 | 0 | 2 | 1 | 0 | 0 |
| AM stiffness (min) | 120 | 15 | 0 | 0 | 0 | 0 | 15 | 15 |
| Grip strength (mm) | | | | | | | | |
| R | 90 | 90 | 135 | 138 | 138 | 128 | 130 | 136 |
| L | 76 | 82 | 135 | 138 | 138 | 192 | 190 | 186 |
| 50′ walk (sec) | 17 | 13 | 12 | 12 | 12 | 12 | 12 | 13 |
| Pt. global assessment | P | F | VG | VG | F | VG | VG | VG |
| Progress | | B | B | B | | B | Same | Same |
| NSAID | + | + | ↓ | + | + (Motrin) | + (Motrin ×3) | + (Motrin 2 × 3) Right knee Tr. swollen | Same as month 6 |
| Other | | | | | | | | |

TABLE 3-continued

| | PATIENT 3 (NS)* | | | | | | | |
|---|---|---|---|---|---|---|---|---|
| | Month | | | | | | | |
| | 0 | 1 | 2 | 3 | 4 | 5 | 6 | #10 |
| | | | | | date | | | |
| | 4/4/91 | 5/2/91 | 6/6/91 | 7/1/91? | | 9/19/91 | 10/24/91 | 02/20/92 |
| RF (date) | 3/27/91 neg | | | | | neg | | |

*Drug discontinued - MTX
Course I (initial) 4/4/91, final 7/5/91

TABLE 4

| | PATIENT 4 (CO)* | | | | | | | | | |
|---|---|---|---|---|---|---|---|---|---|---|
| | Month | | | | | | | | | |
| | 0 | 1 | 2 | 3 | 4 | 5 | 6 | 7 | 8 | 9 |
| | | | | | | date | | | | |
| | 5/3/91 | 6/3/91 | 7/3/91 | 8/30/91 | | 10/4/91 | 10/25/91 | 11/22/91 | 12/20/91 | 2/03/92 |
| Dose (mg) | | 0.1 | 0.5 | 0.5 | 0 | 0 | 0.5 | 0.5 | 0.5 | 0 |
| No. swollen joints | 8 | 4 | 2 | 0 | 1 | 4 | 10 | 2 | 0 | 0 |
| No. tender joints | 9 | 5 | 2 | 1 | 0 | 6 | 12 | 2 | 0 | 0 |
| AM stiffness (min) | 120 | 120 | 15 | <15 | 0 | 120 | 120 | 30 | <15 | 0 |
| Grip strength (mm) | | | | | | | | | | |
| R | 58 | 45 | 82 | 92 | 70 | 54 | 52 | 45 | 50 | 45 |
| L | 48 | 42 | 68 | 78 | 60 | 50 | 52 | 45 | 52 | 55 |
| 50' walk (sec) | 9 | 9 | 9 | 9 | 10 | 13 | 16 | 13 | 12 | 12 |
| Pt. global assessment | P | P | F | G | VG | F | VP | MB | MB | MB |
| Progress | | Same | B | MB | MB | W | W | VG | VG | VG |
| NSAID | + | + | + (Voltaren) | + (Voltaren) | + (Voltaren) | + (Voltaren 75-bid; Advil) | + (Voltaren) | V-bid | V-bid | V-bid |
| Other | | | | | | | | | energy good | |
| RF (dose) | 4/24/91 1:320 | | | | | 10/9/91 1:5120 | 10/29/91 1:1280 | | | |

*Drug discontinued - MTX
Course I (initial) 5/3/91, final 8/3/91
Course II (initial) 10/25/91, final 1/25/91

EXAMPLE 2

The same preparation dosage and protocol were used as in Example 1. Patients ML, MT, RB, LM, DH and SH suffering from rheumatoid arthritis were given chick type II collagen as in Example 1 and were monitored as in Example 1. All of these patients were also treated in a single-blind manner; their condition was worse than that of the Example 1 patients and their average age was about 9 years higher. One female patient (DH) withdrew because of no progress and inconvenience of travel.

Tables 5-10 summarize the data collected for 6 additional individual patients (5 females, 1 male) involved in a second on-going study on the effectiveness of oral administration of whole type I collagen protein to suppress or cure arthritis. Only patient RB (Table 7) experienced complete recovery. A second patient has withdrawn from the present study. The other patients have not experienced as remarkable a recovery as those patients involved in the first study, tables 1-4. There has been great improvement from arthritis, but the rate of recovery is more gradual. More time is needed to effectively evaluate the effects of the second study, but all of the patients of the second study had much more severe disease than the patients in the first study. Moreover, the second group of patients were generally older than the first (ages were 23, 36, 52, 55, 55 and 65). Nevertheless, patients 5 and 7 benefitted considerably and even patients 8 and 10 were able to discontinue use of cytotoxic drugs.

TABLE 5

| | PATIENT 5 (ML)* | | | | | | | | | |
|---|---|---|---|---|---|---|---|---|---|---|
| | Month | | | | | | | | | |
| | 0 | 1 | 2 | 3 | 4 | 5 | 6 | 7 | 8 | 9 |
| | | | | date | | | | | | |
| | 8/9/91 | 9/5/91 | 10/3/91 | 10/31/91 | | | | | | |
| Dose (mg) | | 0.1 | 0.5 | 0.5 | | | | | | |
| No. swollen joints | 12 | 6 | 5 | 4 | | | | | | |
| No. tender joints | 16 | 6 | 5 | 2 | | | | | | |
| AM stiffness (min) | All day | 120 | 120 | 30 | | | | | | |
| Grip strength (mm) | | | | | | | | | | |
| R | 22 | 44 | 70 | 75 | | | | | | |
| L | 26 | 38 | 45 | 13 | | | | | | |
| 50' walk (sec) | 19 | 15 | 15 | 15 | | | | | | |

TABLE 5-continued

PATIENT 5 (ML)*

| | Month | | | | | | | | | |
|---|---|---|---|---|---|---|---|---|---|---|
| | 0 | 1 | 2 | 3 | 4 | 5 | 6 | 7 | 8 | 9 |
| | | | | date | | | | | | |
| | 8/9/91 | 9/5/91 | 10/3/91 | 10/31/91 | | | | | | |
| Pt. global assessment | VP | P | VG | G | | | | | | |
| Progress | | Same | B | B | | | | | | |
| NSAID | + (Clinoril & Pred) | + | + | decrease Pred-2.5 mg 0-Naprosyn | | | | | | |
| Other | | 0.9 cm module | | | | | | | | |
| RF (date) | 8/5/91 1:5120 | | 10/3/91 1:5120 | 10/31/91 1:5120 | | | | | | |

*Drug discontinued - MTX
Course I (initial) 8/5/91, final 11/2/91

TABLE 6

PATIENT 6 (MT)*

| | Month | | | | | | | | | |
|---|---|---|---|---|---|---|---|---|---|---|
| | 0 | 1 | 2 | 3 | 4 | 5 | 6 | 7 | 8 | 9 |
| | | | | date | | | | | | |
| | 8/21/91 | 9/19/91 | 10/17/91 | 11/13/91 | | | | | | |
| Dose (mg) | | 0.1 | 0.5 | 0.5 | 0 | | | | | |
| No. swollen joints | 12 | 12 | 8 | 7 | | | | | | |
| No. tender joints | 14 | 14 | 10 | 10 | | | | | | |
| AM stiffness (min) | All day | All day | till 2 pm | All day | | | | | | |
| Grip strength (mm) | | | | | | | | | | |
| R | 18 | 28 | 30 | 8 | | | | | | |
| L | 30 | 38 | 35 | 18 | | | | | | |
| 50' walk (sec) | 18 | 18 | 18 | 23 | | | | | | |
| Pt. global assessment | P | P | P | VP | | | | | | |
| Progress | | Same | Same | W | | | | | | |
| NSAID | | Naprosyn (750) | + | +Pred | increase Pred- 5 mg: Naprosyn-375bid | | | | | | |
| Other | | ESR-22 Hct-36 | | | | | | | | |
| RF (date) | | 8/21/91 1:640 | | | 11/13/91 + | | | | | |

*Drug discontinued - MTX-2 wks
Pred-2.5 mg during 0.1-early 0.5, resumed
Course I (initial) 8/21/91, final 11/21/91

TABLE 7

PATIENT 7 (RB)*

| | Month | | | | | | | | | |
|---|---|---|---|---|---|---|---|---|---|---|
| | 0 | 1 | 2 | 3 | 4 | 5 | 6 | 7 | 8 | 9 |
| | | | | date | | | | | | |
| | 8/21/91 | 9/20/91 | 10/18/91 | 12/05/91 | 01/15/92 | | | | | |
| Dose (mg) | | 0.1 | 0.5 | 0.5 | 0 | | | | | |
| No. swollen joints | 14 | 8 | 4 | 1 | 0 | | | | | |
| No. tender joints | 16 | 4 | 6 | 0 | 0 | | | | | |
| AM stiffness (min) | 120 | 90 | 90 | 0 | 60 | | | | | |
| Grip strength (mm) | | | | | | | | | | |
| R | 68 | 92 | 92 | 105 | 95 | | | | | |
| L | 40 | 70 | 70 | 85 | 85 | | | | | |
| 50' walk (sec) | 16 | 11 | 11 | 11 | 11 | | | | | |
| Pt. global assessment | VP | MB | G | VG | VG | | | | | |
| Progress | | MB | Same | B | Same | | | | | |
| NSAID | Naprosyn (1500) | + (1000) | + (1000) (Tyl-3am, 2pm) Pred | + Tyl-2bid Pred-2 mgqd | + Pred- 2 mgqd Nap-55bid | | | | | |
| Other 5mm nodule R-olecranon Pred-3 mg/da | | | 3 mm module | Unchg'd | Same | | | | | |
| RF (date) | 8/21/91 1:5120 | 9/24/91 1:160 | 10/22/91 1:10240 | | | | | | | |

*Drug discontinued - Imuran
Course I (initial) 8/21/91, final 11/21/91

TABLE 8

PATIENT 8 (LM)*

| | Month | | | | | | | | | |
|---|---|---|---|---|---|---|---|---|---|---|
| | 0 | 1 | 2 | 3 | 4 | 5 | 6 | 7 | 8 | 9 |
| | | | | date | | | | | | |
| | 10/3/91 | 11/1/91 | 12/5/91 | 1/9/92 | | | | | | |
| Dose (mg) | | 0.1 | 0.5 | 0.5 | 0 | | | | | |
| No. swollen joints | 10 | 10 | 8 | 9 | | | | | | |
| No. tender joints | 14 | 14 | 10 | 10 | | | | | | |
| AM stiffness (min) | 180 | 120 | 150 | 120 | | | | | | |
| Grip strength (mm) | | | | | | | | | | |
| R | 30 | 52 | 38 | 35 | | | | | | |
| L | 28 | 42 | 28 | 32 | | | | | | |
| 50' walk (sec) | 22 | 23 | 22 | 20 | | | | | | |
| Pt. global assessment | P | P | P | P | | | | | | |
| Progress | | Same | Same | Same | | | | | | |
| NSAID | Naprosyn bid Darvocet | Nap-250bid Darvocet | Nap Darvocet | | | | | | | |
| Other | IA steroids/ both knees 2 wks ago | | | | | | | | | |
| RF (date) | 10/8/91 1:160 | | | | | | | | | |

*Drug discontinued - MTX
Course I (initial) 10/3/91, final 1/3/92

TABLE 9

PATIENT 9 (DH)*

| | Month | | | | | | | | | |
|---|---|---|---|---|---|---|---|---|---|---|
| | 0 | 1 | 2 | 3 | 4 | 5 | 6 | 7 | 8 | 9 |
| | | | | date | | | | | | |
| | 10/23/91 | 11/22/91 | | | | | | | | |
| Dose (mg) | | 0.1 | 0.5 | 0.5 | | | | | | |
| No. swollen joints | 12 | 12 | | Withdrew from trial 1/3/92 | | | | | | |
| No. tender joints | 14 | 13 | | | | | | | | |
| AM stiffness (min) | 240 | 360 | | | | | | | | |
| Grip strength (mm) | | | | | | | | | | |
| R | 50 | 5 | | | | | | | | |
| L | 35 | 10 | | | | | | | | |
| 50' walk (sec) | 23 | in wheel chair | | | | | | | | |
| Pt. global assessment | P | VP | | | | | | | | |
| Progress | | MW | | | | | | | | |
| NSAID | Disalc-750qid Pred-4 mg | Pred increase 10 mg/qid | | | | | | | | |
| Other | | | | | | | | | | |
| RF (date) | neg. | | | | | | | | | |

*Drug discontinued - Mtx,-17.5 mg-off 8 da; had PM fatigue
Course I (initial) 10/24/91, final 1/24/92

TABLE 10

PATIENT 10 (SH)*

| | Month | | | | | | | | | |
|---|---|---|---|---|---|---|---|---|---|---|
| | 0 | 1 | 2 | 3 | 4 | 5 | 6 | 7 | 8 | 9 |
| | | | | date | | | | | | |
| | 10/26/91 | 11/22/91 | 12/19/92 | 2/6/92 | | | | | | |
| Dose (mg) | | 0.1 | 0.5 | 0.5 | | | | | | |
| No. swollen joints | 14 | 11 | 11 | 11 | | | | | | |
| No. tender joints | 16 | 11 | 13 | 13 | | | | | | |
| AM stiffness (min) | 480 | 360 | 360 | 360 | | | | | | |
| Grip strength (mm) | | | | | | | | | | |
| R | 28 | 25 | 12 | 22 | | | | | | |
| L | 30 | 35 | 28 | 26 | | | | | | |
| 50' walk (sec) | 23 (with cane) | 23 | 22 | 22 | | | | | | |
| Pt. global assessment | VP | P | P | P | | | | | | |
| Progress | | Same | Same | Same | | | | | | |
| NSAID | | | | | | | | | | |
| Other | Pred- 10 mgqd | | | Pred decrease | | | | | | |

TABLE 10-continued

| | PATIENT 10 (SH)* | | | | | | | | |
|---|---|---|---|---|---|---|---|---|---|
| | | | Month | | | | | | |
| | 0 | 1 | 2 | 3 | 4 | 5 | 6 | 7 | 8 | 9 |
| | | | | date | | | | | | |
| | 10/26/91 | 11/22/91 | 12/19/92 | 2/6/92 | | | | | | |
| RF (date) | 6 × 500- Disalcid 1:320 | | | 5 mg | | | | | | |

*Drug discontinued - 6-MP
Course I (initial) 10/26/91, final 1/26/91

SUMMARY OF FOLLOW-UP OF PATIENTS IN EXAMPLES 1 and 2

In these open-dosing studies 6 out of 10 patients received a considerable benefit from oral chick type II collagen as measured by reduction or elimination in most clinical symptoms. Three of the 10 patients continue to function at the improved condition without further treatment. Two other patients experienced a relapse but after a single-month resumption of collagen therapy they resumed the improved state. A sixth patient seemed to be improving as well as the first three but follow-up was lost. A seventh patient experienced only a mild improvement and two other patients experienced no improvement but were still able to discontinue cytotoxic drugs. The tenth patient withdrew from the study because of her poor initial condition, absence of improvement and remote location from the study center. Based on these very positive results, a double-blind study has been undertaken.

EXAMPLE 3: COLLAGEN DERIVED PEPTIDES

The collagen-derived peptides synthesized in-house using well-known techniques, specifically using a peptide synthesis apparatus (from Applied Biosystems) and following the supplier's instructions. The peptides had the amino acid sequences:

1. NH$_2$-G-P-R-G-P-HP-G-P-HP-G-P-A-G-L-HP-G-P-K-COOH [SEQ ID NO: 2]
2. NH$_2$-G-E-HP-G-A-HP-G-P-A-G-P-HP-G-E-HP-G-A-HP-G-P-A-G-COOH [SEQ ID NO: 4]
3. NH$_2$-G-E-E-G-L-R-G-A-R-G-E-HP-G-E-R-G-P-HP-G-P-Q-G-A-R-COOH

The standard one-letter abbreviations for amino acids are used above with HP denoting hydroxyproline.

The foregoing peptides 1-3 were designed as follows:
The amino acid sequence of human Type II collagen was divided into amino acid triplets which tend to repeat (identically or with conservative substitutions). It was postulated that frequently occurring triplets would be likely to form T-cell epitopes including immunosuppressive epitopes, consistent with the concept of Bystander Suppression (U.S. patent application Ser. No. 843,752). The length of the peptides was based on the fact that the Class I restricted MHC cleft is 9 amino acids long and the Class II restricted MHC cleft is 15 amino acids long. Frequently occurring triplets were then selected and peptides containing them were synthesized and tested. Hydroxyproline was substituted for proline for convenience of synthesis.

Another peptide, No. 4, was also synthesized. This peptide is disclosed in Myers, L. K. et al., *J. Exp. Med.*, 1989, supra, and has the following sequence:

4. H$_2$N-P-T-G-P-L-G-P-K-G-Q-T-G-E-L-G-I-A-G-F-K-G-E-Q-G-P-K-COOH [SEQ. ID NO: 6]

The foregoing peptides were tested for tolerizing activity as follows: (peptides 1-3 are also referred to as CDP1-CDP3 and peptide 4 is referred to as CB11P).

Lewis rats were variously fed 1, 10, 100 micrograms of a particular peptide or soluble chicken Type II collagen. Negative controls were fed an equal volume JGB buffer (127 mM dibasic potassium phosphate, 18.4 mM monobasic potassium, phosphate, pH adjusted to 7.6).

Peptide, collagen or buffer feedings were made −7, 5, and −2 days prior to adjuvant arthritis (AA) induction by challenge with 0.1 ml of complete Freund's adjuvant containing 10 mg/ml *Mycobacterium tuberculosis*. Arthritis severity was evaluated according to standard methodology, Trentham, D. E. et al., 1977, supra, by observation of each of four paws and grading on an arbitrary scale of 1-4 as follows: 0=normal; 1=redness only; 2=redness plus swelling; 3=severe swelling; and 4=joint deformity. The total arthritis score was the sum of the scores for all paws. Maximum arthritis score was the highest score for an animal over the course of the disease. According to this grading method the highest arthritis score possible is 16 (4 paws×4 score-per-paw).

The results are summarized in FIGS. 1-4.

FIG. 1 shows the suppressive ability of whole collagen.

Figure 2:
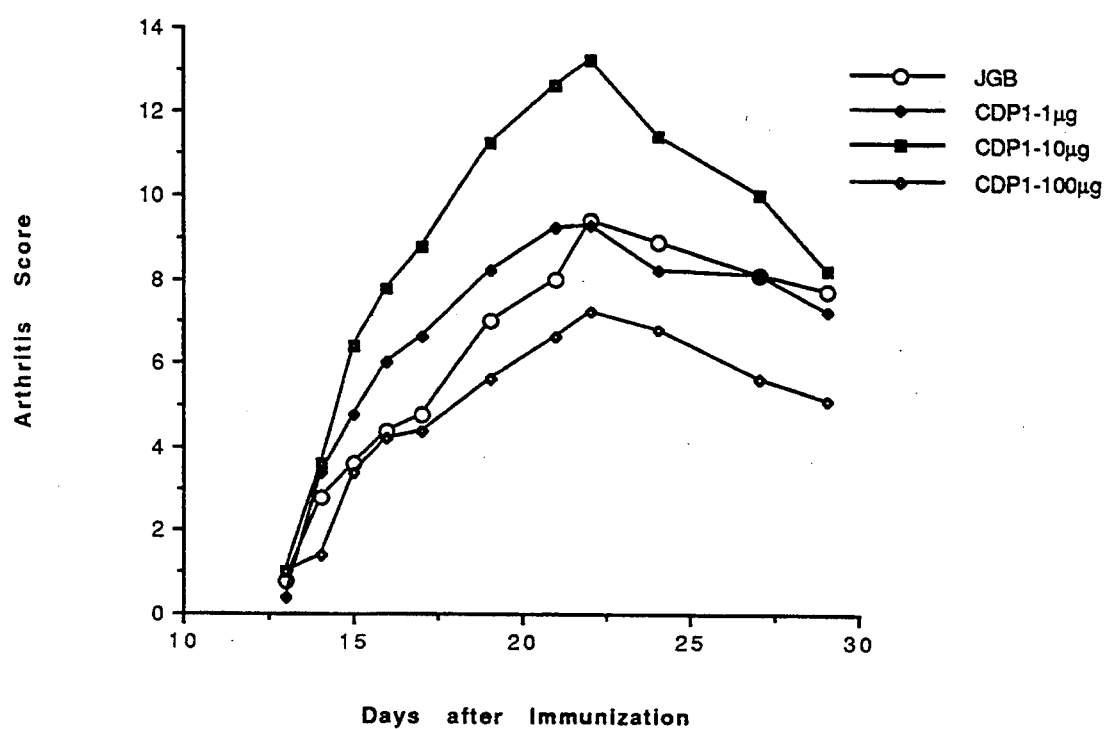
FIG. 2 represents the results of an experiment in which a collagen fragment CDP1 was tested at 1, 10 and 100 pg and showed marked suppression at 100 $\mu$g.

FIG. 2 represents the results of an experiment in which CDP1 was tested at 1, 10 and 100 μg and showed marked suppression at 100 μg.

Figure 3:
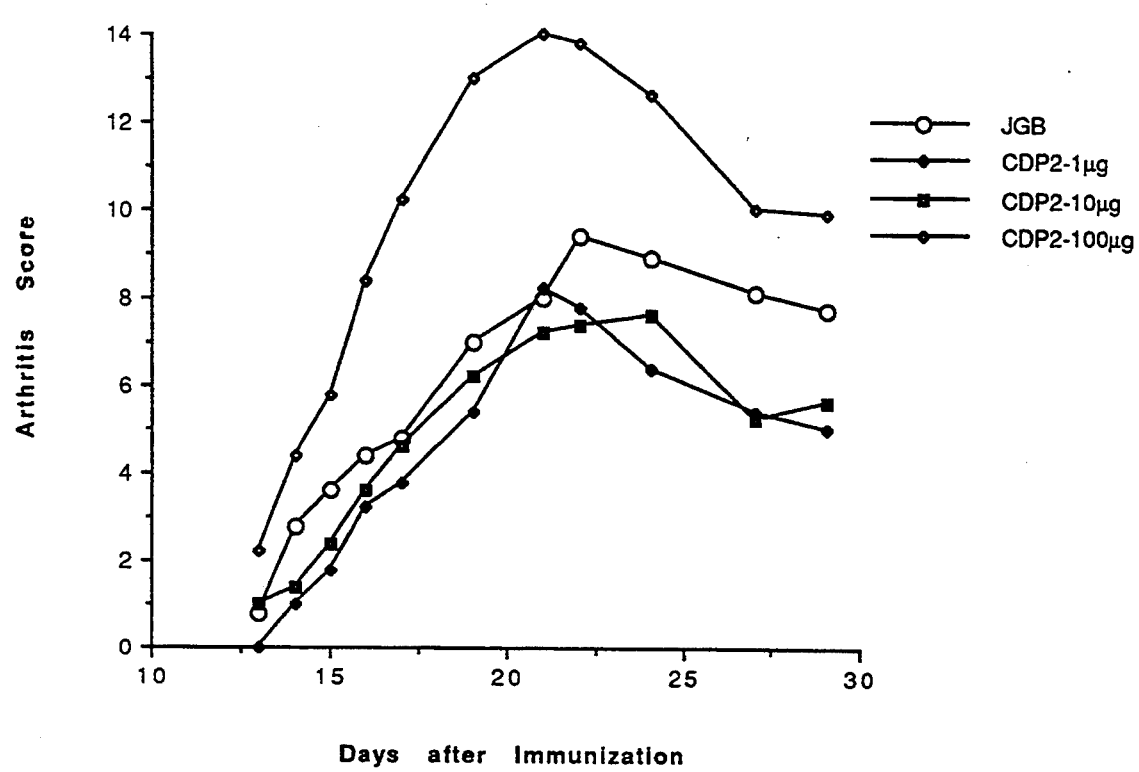
FIG. 3 shows another experiment in which a collagen fragment CDP2 at 1 $\mu$g and 10 $\mu$g induced some suppression, especially at the early stages of AA.

FIG. 3 shows another experiment in which CDP2 at 1 μg and 10 μg induced some suppression, especially at the early stages of AA.

Figure 4:
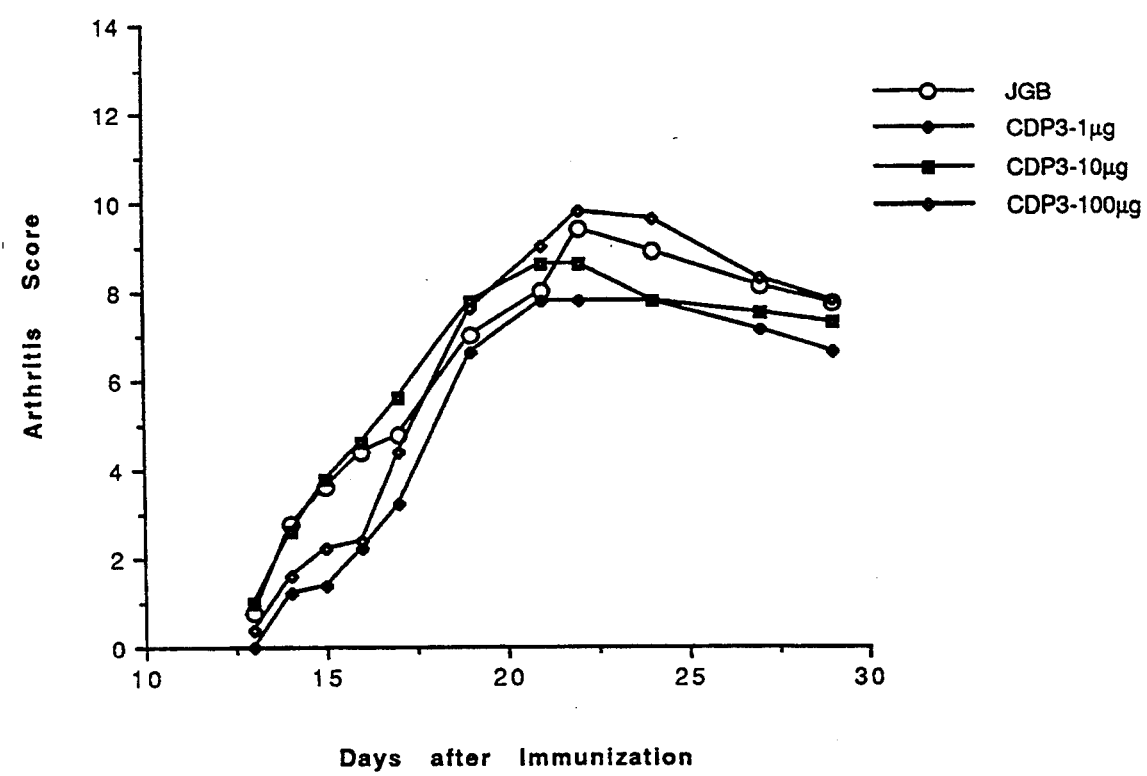
FIG. 4 shows a fourth experiment in which a collagen fragment CDP3 at 1 and 10 $\mu$g induced suppression.

FIG. 4 shows a fourth experiment in which CDP3 at and 10 μg induced suppression.

In summary, CDP1 at 100 μg, CDP2 at 10 and 1 μg and CDP3 at 1 and 10 μg clearly induced some suppression.

Also, in general there was suppression in the peptide-fed rats at the early stages of AA and for certain peptides and dosages the severity of the disease "peaked" earlier, i.e. was milder.

A technical problem with this experiment is that the rats fed buffer did not get very sick, which may be due to a number of technical reasons. Nevertheless, suppression was shown not to require entire CII.

Table 11 below shows the results in terms of arthritis score of the same type of experiment in which the "best" dosage levels of each peptide were used: 100 μg of CDP1; CDP2 at 1 μg; and CDP3 at 1 μg. The Myers et al. peptide, CBll, was also tested at 10 μg.

TABLE 11

| MATERIAL FED | DAY POST-IMMUNIZATION | | | |
|---|---|---|---|---|
| | DAY 20 | DAY 22 | DAY 24 | DAY 27 |
| JGB (−control) | 8.43 ± 1.45 | 8.43 ± 1.45 | 8.43 ± 1.45 | 6.9 ± 1.33 |

TABLE 11-continued

| MATERIAL FED | DAY POST-IMMUNIZATION | | | |
|---|---|---|---|---|
| | DAY 20 | DAY 22 | DAY 24 | DAY 27 |
| CII (+control) | 6.57 ± 1.79 | 6.57 ± 2.20 | 6.42 ± 2.16 | 5.79 ± 2.10 |
| CDP1 | 8.14 ± 1.92 | 8.28 ± 2.06 | 8.42 ± 2.11 | 7.28 ± 2.26 |
| CDP2 | 4.57 ± 0.38 | 4.71 ± 1.52 | 4.71 ± 1.52 | 2.86 ± 0.88 |
| CDP3 | 4.86 ± 2.04 | 4.64 ± 2.02 | 4.64 ± 2.01 | 3.86 ± 1.93 |
| CB11 | 2.86 ± 1.62 | 2.86 ± 1.62 | 2.57 ± 1.67 | 2.29 ± 1.61 |

This experiment shows that CDP2 and CB11 performed best in terms of suppressing adjuvant arthritis. CDP1 did not show marked suppression in this experiment probably due to technical reasons. CDP2 and CDP3 showed substantial suppression. Whole Type II collagen did not suppress as well as expected again probably due to technical reasons. Nevertheless, significant suppression was demonstrated with three peptides (two or more points in the arthritis score is considered significant).

---

We claim:

1. A method for treating rheumatoid arthritis comprising oral administration of whole collagen II protein to a human in need of treatment, in an amount effective and for a period of time sufficient to decrease at least one clinical symptom selected from the group consisting of joint tenderness, joint swelling, morning stiffness, grip strength, and 50-foot walk time.

2. The method of claim 1, wherein the amount is within the range of about 0.1 to about 1 mg/day.

3. The method of claim 2 wherein the effective amount is within the range of about 0.1 to 0.5 mg/day.

4. The method of claim 2 wherein said type II collagen is dissolved in a physiologically acceptable aqueous acidic medium.

5. A method for treating rheumatoid arthritis in a human in need of such treatment comprising oral administration to said human an amount of protein consisting of whole type II collagen, said amount being effective to decrease at least one arthritis symptom.

6. A method for treating rheumatoid arthritis in a human in need of such treatment comprising oral administration of whole type II collagen in an amount effective to suppress autoimmune response in at least one afflicted joint of said human.

7. A method for treating rheumatoid arthritis comprising oral administration of whole collagen II protein to a human in need of such treatment, in an amount effective and for a period of time sufficient to substantially stabilize the arthritic condition while discontinuing cytotoxic drug administration.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Gallus domesticus
        ( F ) TISSUE TYPE: collagen ( x i ) SEQUENCE DESCRIPTION: SEQ ID NO:1:

```
Pro Thr Gly Pro Leu Gly Pro Lys Gly Gln Thr Gly Glu Leu Gly Ile
 1               5                  10                  15
Ala Gly Phe Lys Gly Glu Gln Gly Pro Lys
            20                  25
```

( 2 ) INFORMATION FOR SEQ ID NO:2:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( i x ) FEATURE:
        ( A ) NAME/KEY: Modified-site
        ( B ) LOCATION: 6
        ( D ) OTHER INFORMATION: /label=3Hyp ( i x ) FEATURE:
        ( A ) NAME/KEY: Modified-site
        ( B ) LOCATION: 9
        ( D ) OTHER INFORMATION: /label=3Hyp ( i x ) FEATURE:
        ( A ) NAME/KEY: Modified-site
        ( B ) LOCATION: 15
        ( D ) OTHER INFORMATION: /label=3Hyp ( i x ) FEATURE:
        ( A ) NAME/KEY: Modified-site
        ( B ) LOCATION: 21
        ( D ) OTHER INFORMATION: /label=3Hyp ( x i ) SEQUENCE DESCRIPTION: SEQ ID NO:2:

Gly Pro Arg Gly Pro Pro Gly Pro Pro Gly Pro Ala Gly Leu Pro Gly
1               5               10                      15

Pro Ser Gly Glu Pro Gly Pro Lys
            20

( 2 ) INFORMATION FOR SEQ ID NO:3:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( i x ) FEATURE:
        ( A ) NAME/KEY: Modified-site
        ( B ) LOCATION: 6
        ( D ) OTHER INFORMATION: /label=3Hyp ( i x ) FEATURE:
        ( A ) NAME/KEY: Modified-site
        ( B ) LOCATION: 9
        ( D ) OTHER INFORMATION: /label=3Hyp ( i x ) FEATURE:
        ( A ) NAME/KEY: Modified-site
        ( B ) LOCATION: 15
        ( D ) OTHER INFORMATION: /label=3Hyp ( i x ) FEATURE:
        ( A ) NAME/KEY: Modified-site
        ( B ) LOCATION: 21
        ( D ) OTHER INFORMATION: /label=3Hyp ( x i ) SEQUENCE DESCRIPTION: SEQ ID NO:3:

Gly Pro Arg Gly Pro Pro Gly Pro Pro Gly Pro Ala Gly Leu Pro Gly
1               5               10                      15

Pro Ser Gly Glu Pro Gly Pro Lys
            20

( 2 ) INFORMATION FOR SEQ ID NO:4:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( i x ) FEATURE:
        ( A ) NAME/KEY: Modified-site
        ( B ) LOCATION: 3
        ( D ) OTHER INFORMATION: /label=3Hyp ( i x ) FEATURE:
        ( A ) NAME/KEY: Modified-site
        ( B ) LOCATION: 6
        ( D ) OTHER INFORMATION: /label=3Hyp ( i x ) FEATURE:
        ( A ) NAME/KEY: Modified-site
        ( B ) LOCATION: 12
        ( D ) OTHER INFORMATION: /label=3Hyp ( i x ) FEATURE:
        ( A ) NAME/KEY: Modified-site
        ( B ) LOCATION: 15
        ( D ) OTHER INFORMATION: /label=3Hyp (  i x ) FEATURE:
    ( A ) NAME/KEY: Modified-site
    ( B ) LOCATION: 18
    ( D ) OTHER INFORMATION: /label=3Hyp (  i x ) FEATURE:
    ( A ) NAME/KEY: Modified-site
    ( B ) LOCATION: 24
    ( D ) OTHER INFORMATION: /label=3Hyp ( x i ) SEQUENCE DESCRIPTION: SEQ ID NO:4:

```
Gly Glu Pro Gly Ala Pro Gly Pro Ala Gly Pro Pro Gly Glu Pro Gly
1               5                   10                  15

Ala Pro Gly Pro Ala Gly Pro Pro Gly
                20                  25
```

( 2 ) INFORMATION FOR SEQ ID NO:5:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( i x ) FEATURE:
        ( A ) NAME/KEY: Modified-site
        ( B ) LOCATION: 12
        ( D ) OTHER INFORMATION: /label=3Hyp ( i x ) FEATURE:
        ( A ) NAME/KEY: Modified-site
        ( B ) LOCATION: 18
        ( D ) OTHER INFORMATION: /label=3Hyp ( x i ) SEQUENCE DESCRIPTION: SEQ ID NO:5:

```
Gly Glu Glu Gly Leu Arg Gly Ala Arg Gly Glu Pro Gly Glu Arg Gly
1               5                   10                  15

Pro Pro Gly Pro Gln Gly Ala Arg
                20
```

( 2 ) INFORMATION FOR SEQ ID NO:6:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:6:

```
Pro Thr Gly Pro Leu Gly Pro Lys Gly Gln Thr Gly Glu Leu Gly Ile
1               5                   10                  15

Ala Gly Phe Lys Gly Glu Gln Gly Pro Lys
                20                  25
```